United States Patent [19]

Becker et al.

[11] 4,251,305
[45] Feb. 17, 1981

[54] METHOD OF RADIANT HEAT SEALING OF A BALLOON ONTO A CATHETER EMPLOYING TINTED SHRINK TUBING

[75] Inventors: Lawrence F. Becker, Chicago; Richard W. Cobean, Libertyville, both of Ill.

[73] Assignee: Baxter Travenol Laboratories, Inc., Deerfield, Ill.

[21] Appl. No.: 956,590

[22] Filed: Nov. 1, 1978

[51] Int. Cl.³ .................... B29C 27/00; B32B 31/00; A61H 25/00
[52] U.S. Cl. ......................... 156/86; 156/272; 156/289; 156/292; 156/294; 156/359; 156/380; 128/349 B
[58] Field of Search ........ 128/349 R, 349 B, 349 BV; 156/84–86, 272, 289, 293, 294, 292, 1

[56] References Cited

U.S. PATENT DOCUMENTS

| | | | |
|---|---|---|---|
| 3,528,869 | 9/1970 | Dereniuk | 156/294 |
| 3,625,793 | 12/1971 | Sheridan et al. | 156/294 X |
| 3,694,280 | 9/1972 | Hoef | 156/84 X |
| 3,832,253 | 8/1974 | Di Palma et al. | 156/86 |
| 3,850,720 | 11/1974 | Collins | 128/349 B X |
| 4,025,378 | 5/1977 | Amsden et al. | 156/272 |
| 4,154,244 | 5/1979 | Becker et al. | 156/294 X |
| 4,198,983 | 4/1980 | Becker et al. | 128/349 B |

Primary Examiner—John T. Goulkasian
Assistant Examiner—Lois E. Rodgers
Attorney, Agent, or Firm—Paul C. Flattery; John A. Caruso; Eugene M. Cummings

[57] ABSTRACT

A thermoplastic member such as a length of tubing for forming a catheter balloon is positioned on the thermoplastic shaft of a medical device. A length of shrink tubing is placed over each end of the balloon tubing and adjoins a portion of the shaft. Each length of shrink tubing may then be preshrunk to maintain its position. The shaft, balloon tubing, and shrink tubing are then inserted in an apparatus capable of supplying radiant heat in a narrow annular band. The apparatus automatically positions each portion of the shaft and balloon tubing covered by shrink tubing at a location at which it will intercept the narrow annular band of radiant heat. Radiant heat is supplied by the apparatus to cause further shrinkage of the shrink tubing and to seal the balloon tubing onto the shaft. The shrink tubing may be removed to complete the assembly of a balloon catheter. It is preferred that the shrink tubing be tinted so as to enhance the seal formed between the balloon tubing and the shaft.

19 Claims, 9 Drawing Figures

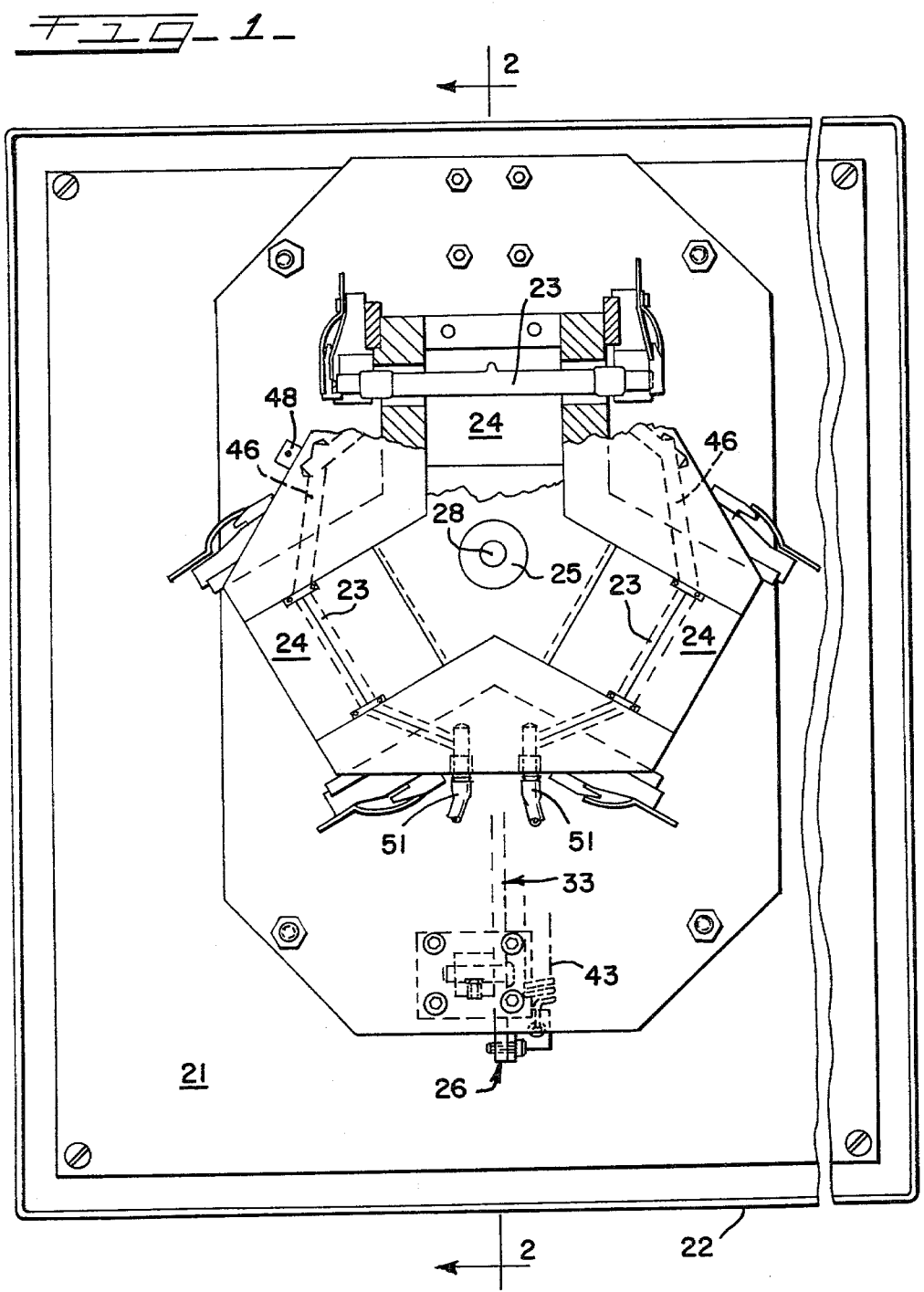

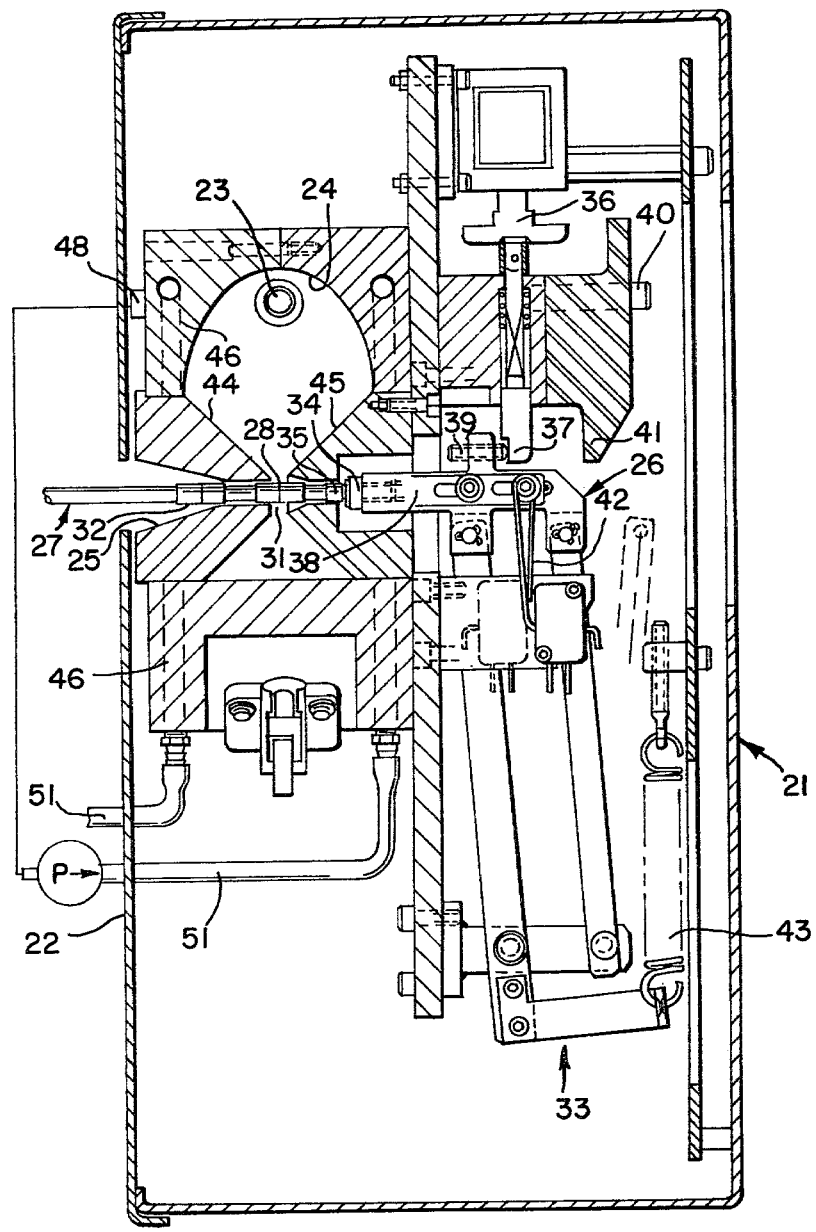
FIG_2

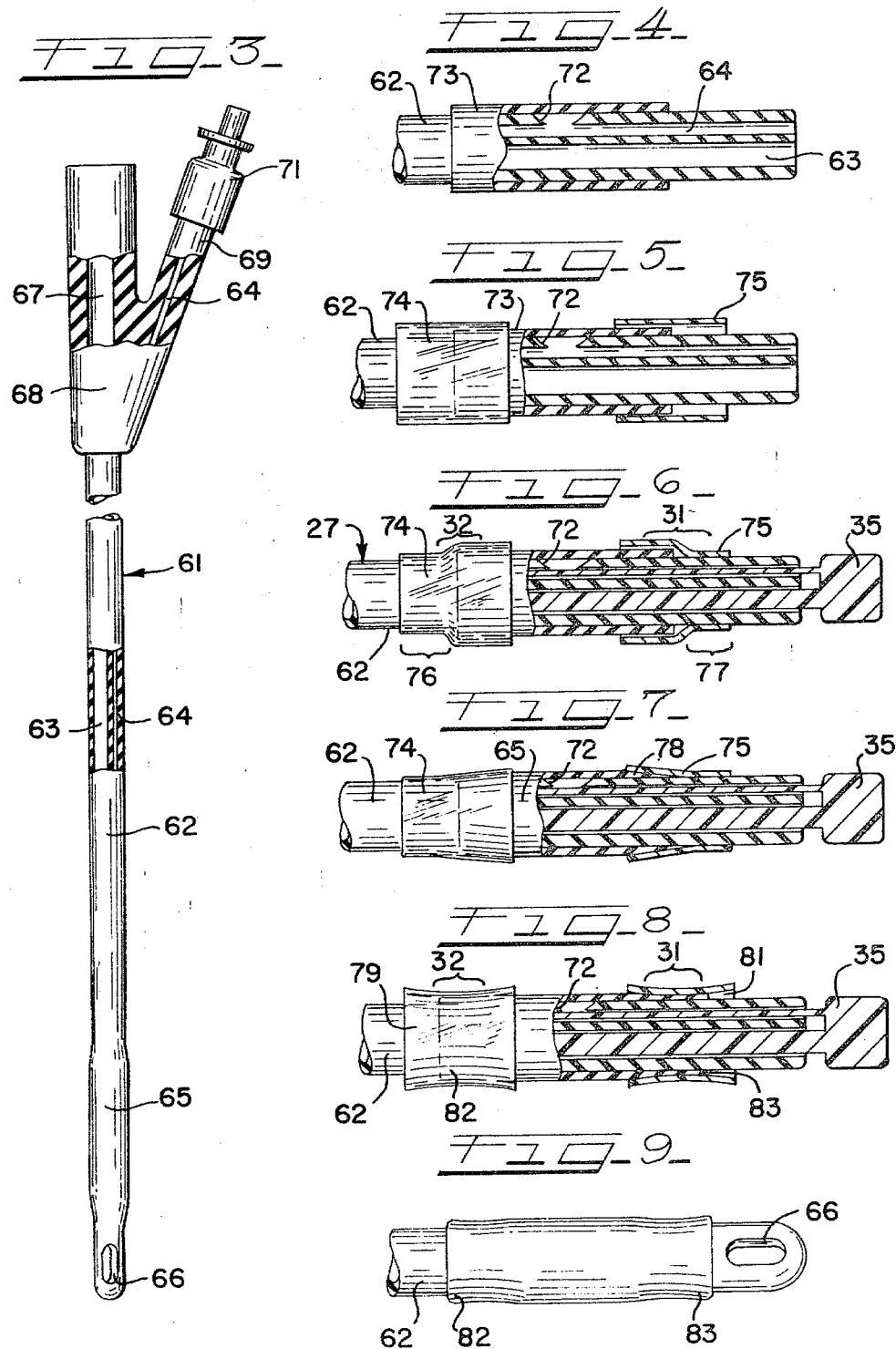

METHOD OF RADIANT HEAT SEALING OF A BALLOON ONTO A CATHETER EMPLOYING TINTED SHRINK TUBING

BACKGROUND AND DESCRIPTION OF THE INVENTION

The present invention relates generally to providing seals along shafts of medical devices by means of radiant energy and is especially suitable for seals of catheter balloons onto catheter shafts. Various aspects of the invention include a radiant energy sealing apparatus as a means for rapidly forming finished medical device products while precisely and automatically aligning the energy emission at desired locations on the product, a method of manufacturing these medical devices through the use of shrink tubing, and a particularly advantageous shrink means for use in conjunction with the apparatus and the method.

Balloon catheters and other medical devices having overlying cylindrical members must develop smooth and secure annular seals or bonds between different assembly parts. In the case of balloon catheters, the balloon is initially an assembly part in the form of an overlying cylindrical member that has to be very securely sealed onto the cylindrical shaft of the catheter near its head. Upon completion of the catheter, the balloon is inflatable so as to make possible, in the case of a Foley catheter for example, retention of the catheter head within the bladder of a patient whereby body fluids can be drained therefrom through the urethra via a lumen through the catheter shaft. Seals for this purpose should be accurately formed, should be as smoothly tapered as possible, and should present very low adulteration risks in order to minimize the chances of patient trauma and urinary tract irritation.

Long used in manufacturing such catheters and the like has been natural rubber latex which is low in cost and has the assembly advantage that the balloon and shaft can be molded in one piece, but which material has come under criticism because of the belief that when devices made therefrom are left within the patient for longer than a day or so, reactions develop with tissue adjacent the catheter that can lead to considerable patient discomfort.

Manufacturing such medical devices from materials other than natural rubber latex or the like generally necessitates a two-piece assembly of the balloon cylinder to the catheter shaft, which assembly can be carried out by such general approaches as bonding the balloon to the shaft with an adhesive, by heat sealing a thermoplastic balloon to a thermoplastic shaft, or by combining adhesives with heat sealing. Adhesives are used for silicone rubber devices but they are usually best avoided because of the additional handling steps and time needed during manufacture and because of potential adulteration risks associated generally with the use of adhesives in medical equipment. Radio frequency heating is generally unsatisfactory because of the need to contact the parts being sealed which deforms the surface and does not allow ready transfer of heat to the interface between the parts, and because of non-uniformity of surface and seal. The use of radiant energy and thermoplastic materials for medical devices to be heat sealed are mentioned in U.S. Patent Application Ser. No. 853,738, filed Nov. 21, 1977, U.S. Pat. Nos. 4,154,244, and 900,965, filed Apr. 28, 1978, U.S. Pat. No. 4,198,983, the disclosures thereof being incorporated by reference herein.

Heretofore, heat sealing techniques, even those avoiding contact between the surface being sealed and the bonding apparatus, have not proven entirely successful. Non-contact radiant energy sealing has been observed to be generally inconsistent in its ability to thoroughly and securely seal balloons to the shafts of catheters throughout the entire annular extent of the seals. A catheter balloon must have no weak points at which the fluid under pressure will slowly dissipate from the balloon when in the environment of the body tissue, which can lead to patient discomfort and occasionally dislodgement from its intended location within the body of the patient.

The present invention provides a method, a shrink tubing means, and an apparatus for forming the types of seals required to meet these needs. Method steps in accordance with this invention include the use of shrink tubing to hold the balloon in place and simultaneously assist in shaping smooth seals, which method includes preshrinking the shrink tubing into place. Preferably, in close association with this method is a shrink tubing means that has been discovered to be especially useful in connection with the forming of extremely secure and consistent sealing throughout the entire annular extent of the radiant energy seal. The apparatus of the present invention provides a uniform annular band of radiant energy to be supplied according to the method of this invention, which radiant energy is transmitted through the shrink tubing means according to this invention. In a preferred aspect of the invention, tinted lengths of shrink tubing are placed over the annular locations to be sealed along the catheter shaft, the shrink tubing is preshrunk along a predetermined length thereof, and the head end of the catheter is then inserted into the apparatus whereupon it is automatically aligned to the proper location along the shaft, radiant energy is applied, and the apparatus then automatically aligns the shaft to the next location therealong, after which further heat sealing treatment is carried out in order to complete the seal at another location along the shaft.

It is accordingly a general object of the present invention to provide an improved method, means, and apparatus for preparing medical devices having overlapping members to be sealed together.

Another object of the present invention is an improved apparatus, means and method for assembling a cylindrical balloon to a balloon catheter or the like in a manner that forms a uniform and secure annular seal that is smoothly tapered for the avoidance of unnecessary trauma to the patient being treated with the device.

Another object of this invention is an improved method, means and apparatus for forming an annular seal between thermoplastic materials, which seal is extremely secure and smoothly tapered as between a cylindrical shaft and an overlying cylindrical balloon.

Another object of the present invention is an apparatus and its associated method whereby precise locations along a cylindrical shaft are subjected to an annular ring of radiant energy and automatically indexed to the next location.

Another object of the present invention is an improved shrink tubing means for forming radiant energy heat seals that are especially secure and well tapered in association with the method of this invention, which means precisely transmits and directs appropriate heat sources in order to optimize the effectiveness of the heat source in producing an extremely secure and consistent seal.

Another object of the present invention is an improved apparatus, method and means for producing balloon catheters and the like with minimal assembly operator involvement and in an extremely short length of time to minimize the amount of heat conducted away to the material surrounding the bond zone, leading to less heat distortion and possible chemical changes in the material.

Other objects of the present invention will be apparent from the following detailed description, taken in conjunction with the accompanying drawings wherein:

FIG. 1 is a top plan view, partially broken away, of the preferred apparatus according to this invention;

FIG. 2 is a sectional view of the preferred apparatus, generally along the line 2—2 of FIG. 1;

FIG. 3 is an elevational view, partially broken away and partially in longitudinal section, of a Foley catheter made in accordance with this invention;

FIG. 4 is an elevational view, partially in longitudinal section, of the head end of an unfinished cathether having a length of tubing over an unfinished head end, the tubing for forming a catheter balloon sealed to the shaft;

FIG. 5 is an elevational view, partially in longitudinal section, of the unfinished catheter head end as shown in FIG. 4, with two lengths of shrink tubing having been slid thereover;

FIG. 6 is an elevational view, partially in longitudinal section, of the unfinished catheter head end of FIGS. 4 and 5, illustrating the preshrinking step in accordance with this invention;

FIG. 7 is an elevational view, in partial longitudinal section, of the catheter head shown in FIGS. 4–6, illustrated after completion of the radiant energy seal and prior to removing the shrink tubing and finishing the tip of the head to form the catheter head end shown in FIG. 3;

FIG. 8 is an elevational view, partially in longitudinal section, of an unfinished catheter head showing a heat seal not in accordance with this invention and assembled according to a method not including a preshrinking step; and FIG. 9 is an elevational view of a finished catheter head made by the method and means illustrated in FIG. 8, and not according to the present invention.

The apparatus illustrated in FIGS. 1 and 2, designated generally by 21, has a case 22, a plurality of sources of radiant energy or lamps 23, a plurality of curved reflectors 24 associated with each lamp 23, a shaft receiving opening 25, and a shaft depth indexing means, generally designated 26. Shown inserted into the opening 25 is the head portion of an unfinished catheter 27 which, prior to treatment within the apparatus 21, is at the stage generally illustrated in FIG. 6. Apparatus 21 automatically indexes the unfinished catheter 27 such that the locations to be sealed with radiant energy will be precisely aligned with a cylindrical treatment site 28 at which is developed a concentrated and focused band of radiant energy emanating from lamps 23 and reflectors 24.

A first portion 31 of the unfinished catheter 27 is subjected to the band of radiant energy at the cylindrical treatment site 28. Movement to a second portion 32 of the unfinished catheter 27 is accomplished through the operation of the shaft depth indexing means 26. More particularly, means 26 includes upwardly biased linkage, generally designated 33, to urge a top switch 34 upwardly for engagement with a stylet 35 inserted into lumens of the unfinished catheter 27. When switch 34 is activated by contact with stylet 35, a timer is activated for transmitting radiant energy sealing power to the lamps 23 for a predetermined length of time, after which the timer also activates a solenoid 36 to withdraw an upper stop 37 from its operative interengagement with the top switch 34 through an arm 38 and an adjustable pin 39. With upper stop 37 withdrawn it is then possible to further insert the unfinished catheter 27 through the shaft receiving opening 25, in opposition to the bias provided by linkage means 33, so as to move arm 38 downwardly until pin 39 engages a lower stop 41, at which time the second portion 32 of the unfinished catheter 27 will be aligned with the cylindrical treatment site 28, which alignment can be facilitated by an adjustor screw 40. As the adjustable pin 39 engages the lower stop 41, a bottom-switch 42 is closed to operate a timer to again provide heat sealing energy to the lamps 23 for a predetermined length of time.

This completes the heat sealing operation, and the unfinished but sealed catheter 27 is then withdrawn through the shaft receiving opening 25, at which time the top switch 34 will return to its initial position shown in FIG. 2 by the force supplied by a biasing means 43 through the linkage means 33. Complete withdrawal of the catheter 27 releases the top switch 34 which results in replacement of the upper stop 37 to its stop position shown in FIG. 2.

In the preferred embodiment of apparatus 21 as illustrated in FIGS. 1 and 2, three lamps 23 are mounted within three reflectors 24 located 120° between each other to provide radiant energy that is substantially uniform throughout the cylindrical treatment site 28, which even heating is enhanced by overlapping reflection patterns emanating from the reflectors 24, which patterns include reflected oblique rays, thereby eliminating any need to rotate the catheter 27. Other configurations are possible, such as having four lamps that are 90° apart from each other, in which case a greater intensity of radiation could be provided for sealing.

Lamps 24 emit energy in the form of visible and infrared light for absorption at the first portion 31 and the second portion 32 of catheter 27. It is preferred, in order to reduce electrical inrush current and heating time variation, that the filaments of the lamps 23 be kept warm on standby at a voltage of about five percent of the rated lamp voltage in between the times that the lamps are provided with full radiant energy sealing power when activated by contact of the top switch 34 and the bottom switch 42. Preferably, each lamp has a very small and very hot filament in order to provide especially accurate focusing of the radiant energy emanating therefrom. A typical acceptable filament diameter is on the order of 1/16 inch.

Preferred reflectors 24 are highly polished metal and have a precise elliptical shape in longitudinal cross section as shown in FIG. 2, with each lamp 23 being located along foci of the respective ellipses. These elliptical surfaces are preferably opposite generally conical secondary reflector surfaces 44, 45. By this arrangement of the reflectors 24, 44 and 45, about two thirds of the radiant energy supplied by the lamps 23 is delivered to the other focus of each respective ellipse, these other foci being generally located along the cylindrical treatment band or site 28.

It is usually advantageous to have the apparatus 21 operate at equilibrium conditions, which can be generally achieved through the use of a cooling means by which a liquid, typically water, at approximately room or ambient temperature is cycled through jackets 46 in the reflectors 24. This cooling fluid is passed through each jacket 46 by way of a pump means 47 that is controlled by a thermostat 48. The preferred mode of operation of the cooling means includes an initial calibration run to determine the appropriate sealing temperature to be developed and to set the thermostat 48 accordingly. Then, as the temperature at thermostat 48 rises above this preset temperature, the thermostat 48 activates pump means 47 to pass the cooling fluid into and through jackets 46. When the temperature at thermostat 48 falls below the preset temperature, the thermostat 48 will shut off the pump means 47, allowing the cooling fluid to stop flowing through jackets 46 and conduit means 51.

The preferred catheter made in accordance with this invention, generally designated 61, is shown in FIG. 3. Catheter 61 includes an elongated shaft 62 having a fluid draining lumen 63 and an inflation lumen 64 which are conventional structures for providing a drainage path from the bladder or the like and for inflating the balloon portion 65 for securing it therewithin, respectively. More particularly, when catheter 61 is inserted into the patient, body fluids leave the patient by way of a port 66, pass through the fluid drainage lumen 63 and an outlet conduit 67 located within a branched connector 68 for passage to an aspirator or other conventional collection means. Branched connector 68 also includes a branch 69 having a valve 71 to receive the luer of a syringe (not shown) and to allow the syringe to place pressurized fluid such as sterile water or air into the inflation lumen 64 for inflation of the balloon portion 65 by passing through an opening 72 (FIG. 4) in the wall of the shaft 62 beneath the balloon portion 65. The valve 71 is structured to retain the fluid pressure after the syringe is withdrawn, the valve being conventional for use on a Foley catheter.

FIG. 4 illustrates an initial step in the preferred catheter balloon assembly method in accordance with this invention. A length of thin-walled tubing 73 is slid over the elongated shaft 62 so that it overlies the wall opening 72. The next step is shown in FIG. 5 whereby one or more lengths of shrink tubing, preferably two lengths of shrink tubing 74, 75 are installed over the thin-walled tubing 73 so as to have approximately half of its length overlap the elongated shaft 62. It will be noted that, because of the difference in diameters between the elongated shaft 62 and the shrink tubing 74, 75, there is a gap between the elongated shaft 62 and each of the lengths of shrink tubing 74, 75.

FIG. 6 illustrates the step of preshrinking the shrink tubing 74, 75, which step is an important feature of this invention. Basically, each length of tubing 74, 75 is subjected to an environment including an elevated temperature at which tubing 74, 75 will partially shrink in diameter, which preshrinking temperature is lower than that which will bring about maximum diameter shrinkage. This preshrinking step has a major objective of removing these gaps between the elongated shaft 62 and the shrink tubing 74, 75. Preferably, this is accomplished by selectively preshrinking the lengths of shrink tubing 74, 75 by concentrating the preshrinking energy at the section of each shrink tubing 74, 75 that overlaps the elongated shaft 62, such selective preshrinking typically being concentrated along circumferential bands illustrated at 76 and 77.

Also shown on FIG. 6 are the first and second portion, 31, 32 of the unfinished catheter 27 which are subjected to radiant energy, preferably at a cylindrical treatment site 28 of apparatus 21 (FIGS. 1 and 2). It is to be noted that the stylet 35 provides support for both fluid drainage lumen 63 and inflation lumen 64 during the preshrinking and radiant energy applying steps so as to prevent collapse or deformation of these two lumens that could be brought about by the elevated temperatures associated with each step. During the radiant energy applying step, the focused energy from lamps 23 strikes first and second portions 31, 32, whereupon the shrink tubing 74, 75 further shrinks and the tubing 73 and shaft 62 are subjected to a temperature in their thermoplastic melting ranges whereby the tubing 73 is softened, shaped, and thermoplastically bonded to the softened shaft 62 into a smooth and gradually tapering thermoplastic joint 78 which has a trailing edge that is generally flush with the outside surface of the elongated shaft 62 as is illustrated in FIG. 7 and as is illustrated in FIG. 3 after the shrink tubing 74, 75 has been removed.

FIGS. 8 and 9 illustrate the results typically realized when the preshrinking step is omitted, the illustration being somewhat exaggerated for drawing clarity. In this case, the elongated shaft having the thin-walled tubing 73 and the lengths of shrink tubing 74, 75 located thereon, generally as shown in FIG. 5, is inserted into the apparatus 21 and serially treated in substantially the same manner as this invention at the first portion 31 and the second portion 32; however, since the lengths of shrink tubing have not been preshrunk, they develop their greatest annular shrinkage in the central portion thereof to have the general configuration of lengths 79, 81, thereby causing the extreme ends of the thin-walled tubing 73 to flow in the direction of these extreme ends and generally into the gaps between the elongated shaft 62 and the non-preshrunk shrink tubing lengths 79, 81, which brings about formation of annular flanges 82, 83, which are undesirable from the point of view of causing trauma and discomfort to the patient. Also, when these seals are formed with irregularities such as the flanges 82, 83, this has generally been found to result in seals between the balloon and the catheter shaft that are not as uniformly formed or as secure as the gradually tapering joints 78. Joints 78 exhibit enhanced mechanical strength and resistance to peel back which would result from irregularities where failure of the bond could initiate.

With more particular reference to the method of this invention, especially to the means and materials used in practicing the same, the catheter shaft 62 is extruded of a material that is typically a thermoplastic one having a characteristic thermoplastic melting range. A typical characteristic range is between 350° and 450° F. It is usually most convenient that the thin-walled tubing 73 for forming the balloon be made of substantially the same material as the catheter shaft, although this is not a requirement provided the shaft and balloon materials are compatible, will soften in the radiant energy applying temperature range, and will form a good thermoplastic bond with each other.

Materials for the catheter and balloon should be acceptable for use within a patient for periods of time between about one day and about one week, for which lengths of time the materials should exhibit very low toxicity so that little or no irritation is experienced by the patient. These materials should exhibit limited friction with body tissue and a significantly reduced tendency to collect encrustation by providing a surface that exhibits a high degree of smoothness and gloss. Suitable materials preferably should have a cost on the order of that of natural rubber latex while being as non-toxic as silicone rubber. Such materials should also be capable of simple extrusion without a postcure time, and should exhibit a thermoplastic softening temperature high enough to permit autoclaving of the finished catheter if desired. The tubing material should be kink and collapse resistant at typical wall thicknesses so as to withstand aspiration during normal use. If possible, the thin-walled tubing for making the balloon may have especially acceptable elastomeric recovery properties and low creep properties so as to reduce the formation of wrinkles upon deflation of the balloon.

When the catheter and balloon unfinished head end is treated by the method and apparatus of this invention, much of the visible and infrared radiation penetrates the balloon-forming tubing, even though it is usually white pigmented and opaque to visible light, which radiation is absorbed below the surface so that the sealing or welding interface is hotter than the surface, a feature that promotes excellent bond formation.

The precise materials suitable for use in this regard can be among those mentioned in said co-pending applications, such as oil-filled thermoplastic rubber materials, and those including a composition of a thermoplastic rubber block copolymer, a crosslinkable organic silicone elastomer and a hydrophobic oil-type plasticizer, the plasticizer being for imparting softness to the elastomeric composition. Also, a material such as a silicone product that is not thermoplastic could be used in conjunction with the placing of a heat curable adhesive between the shaft and the balloon member, such adhesives being of the type that exhibit accelerated cure when heated.

The shrink tubing 74, 75, is made of a material that will shrink upon being subjected to heat. For use in accordance with this invention, the material should exhibit a preshrinking characteristic whereby it will partially shrink under conditions that will not substantially deform the underlying substrate and will shrink further when subsequently subjected to higher temperatures than those characteristic of the partial shrink or preshrink stage. Also, the shrink tubing material should not develop pinholes or melt upon being exposed to the temperatures and conditions necessary to heat seal the balloon member to the shaft.

These shrink tubing materials should not adhere to any substantial degree to the shaft and balloon materials being shaped and bonded. Preferably, such materials will shrink only in a annular manner whereby they are uniformly reduced throughout the circumference, but they will not shrink longitudinally which would lead to shrivelling and a deformed bond. A further particularly advantageous feature to be exhibited by the shrink tubing material is having the ability to be tinted.

Materials that have been found to possess substantially all of these features are fluorinated polyolefin materials, such as fluorinated ethylene propylene (fep) which has a particularly advantageous set of two-stage shrinking temperatures, tetrafluoroethylene, which has a set of temperature ranges somewhat higher than fep, and copolymers of ethylene and tetrafluoroethylene, which usually have a set of shrink temperatures generally lower than fep.

Fep is particularly preferred because it is transparent and has excellent release characteristics, because it will not melt until reaching temperatures above about 450° F. under the conditions of this invention, and because it has an initial preshrink temperature of about 250° F. and full shrink temperature range between about 350° and 450° F.

Especially advantageous results are achieved when the shrink tubing is tinted with a pigment or the like, which has unexpectedly been found to increase the rate of bond formation and to further enhance the uniformity of the annular shrink properties of such tubing. For example, when comparing the use of untinted fep shrink tubing with the use of appropriately tinted fep tubing under the same conditions and for bonding the same materials, the preshrinking was completed in a time period about 25% less than the time required for the untinted tubing, and the subsequent sealing time was reduced to even a greater degree, the untinted taking about 1.8 seconds and the tinted tubing taking only 1.2 seconds to complete formation of the tapered bond. Additionally, the untinted material was found to result in balloon-to-shaft bonds that had some weak points at spaced locations around the bond.

While we do not wish to be bound by any theory, it is believed that the pigment within the shrink tubing may scatter the radiant energy to generate additional heat under the shrink tubing. It is additionally believed that metal within the pigment might bring about a more efficient heat transfer, which could be a reason why tinted shrink tubing improves a preshrinking step which uses only a source of hot air to provide the preshrink environment, no radiation energy being employed.

The amount of tinting employed should be in a range so that the tint is faint enough that most of the radiant energy passes through the shrink tubing and is used to directly heat the balloon member and the shaft; yet the amount of tinting must be substantial enough to realize the advantageous results in accordance with this aspect of the invention often indicated by a noticeable slight warming of the shrink tubing itself. If the tinting is too great, too much heat will be developed in the shrink tubing and swelling of the bond will occur, resulting in a deformed product. Broadly speaking, the tinting range will provide a tinted shrink tubing having a characteristic lower tinting limit slightly above transparency and an upper tinting limit approaching translucency. The upper limit will be less than that of opacity, typically occurring at a weight percent range of about 0.5 weight percent of pigment based on the total weight of the shrink tubing composition. A usual range within which many pigments develop suitable tinting of fluorinated polyolefin materials is between about 0.01 and about 0.1 weight percent, based upon the total weight of the shrink tubing. The most advantageous pigment concentration will vary, of course, with the pigment used and with the material being tinted.

When the pigment contains a metal, it preferably should not be a heavy metal in order to reduce any possible toxicity risks. Preferred pigments should exhibit a flat reflectance curve so that low reflectance, on the order of 1 percent, is generally uniformly observed substantially throughout the entire wavelength range, from ultraviolet through infrared. A particularly acceptable shrink tubing is a formulation of fep with 0.025 weight percent of a black inorganic pigment formed into shrink tubing having a wall thickness of about 11 thousandths of an inch, which has been employed in this invention and has been found to reduce the preshrinking time by about 25 percent and reduce the bonding time by about ⅓ when compared with non-tinted fep, while exhibiting a shrink that is more uniform than and a balloon-to-shaft seal that is stronger than that obtained with non-tinted fep.

It will be apparent to those skilled in this art that the present invention can be embodied in various forms; accordingly, this invention is to be construed and limited only by the scope of the appended claims.

We claim:

1. A method for using radiant energy for sealing annular ends of a tubular member onto an elongated shaft of a medical device, comprising:
   sliding the tubular member over an unfinished elongated shaft of the medical device;
   installing a length of tinted shrink tubing to overlie at least a part of both the shaft and the tubular member to form first and second portions that include at least a part of the shrink tubing and of the shaft and tubular member thereunder;
   preshrinking said tinted shrink tubing while installed to overlie at least a part of both the shaft and tubular member;
   inserting the unfinished shaft including said first and second portions into an enclosure having a cylindrical treatment site providing a band of radiant energy; and
   aligning said first and second portions of the unfinished shaft with said band of radiant energy at the cylindrical treatment site for sealing the annular ends of the tubular member to the shaft.

2. The method of claim 1, further comprising passing a stylet into a lumen of said elongated shaft prior to said inserting step in order to avoid closing the lumen.

3. The method of claim 1, wherein said preshrinking step is a selective preshrinking step by concentrating energy for such step only at the section of shrink tubing that overlaps the elongated shaft and does not significantly overlap the installed tubular member.

4. The method of claim 1, wherein said preshrinking step includes substantially closing a gap between the shrink tubing and the shaft.

5. The method of claim 1, wherein said sealing of the annular ends of the tubular member to the shaft includes softening and shaping the tubular member, softening the shaft, and bonding the softened and shaped tubular member to the softened shaft.

6. The method of claim 1, wherein said preshrinking step is at a temperature between about 200° F. and about 350° F., and wherein said sealing is at a temperature of between about 350° F. and about 450° F.

7. The method of claim 1, wherein the band of radiant energy penetrates to a bonding interface between the tubular member and the elongated shaft.

8. The method of claim 1, further comprising providing shrink tubing that shrinks substantially only in an annular manner to be uniformly reduced throughout its circumference.

9. The method of claim 1, further comprising providing shrink tubing of a fluorinated polyolefin material.

10. The method of claim 1, wherein said tinted shrink tubing increases the rate of sealing and enhances the strength and consistency of sealing.

11. The method of claim 1, wherein said tinted shrink tubing is tinted by incorporating an amount of pigment thereinto, said amount providing a tinted shrink tubing having a characteristic lower tinting limit slightly above transparency and an upper tinting limit approaching translucency.

12. The method of claim 1, wherein said sliding step and said sealing step are carried out with a tubular member that is thin-walled.

13. The method of claim 1, further comprising placing a heat curable adhesive between the shaft and the tubular member.

14. The method of claim 1, further comprising removing the shrink tubing from the shaft after the sealing step.

15. A method of sealing annular ends of a tubular member onto an elongated shaft of a medical device comprising the steps of:
   sliding the tubular member over an unfinished elongated shaft of the medical device;
   installing two lengths of tinted shrink tubing, one length at each end of said tubular member to overlie a part of both the shaft and the tubular member to form first and second portions that include at least a part of the shrink tubing and of the shaft and tubular member thereunder;
   preshrinking said tinted shrink tubing while it is installed to overlie part of both the shaft and the tubular member;
   inserting the unfinished shaft including said portions into an enclosure having a cylindrical treatment site capable of providing a band of radiant energy;
   aligning said first and second portions of the unfinished shaft at a location in said cylindrical treatment site for sealing the annular ends of the tubular member to the shaft with said band of radiant energy; and
   applying said radiant energy at said first and second portions thereby sealing the annular ends of said tubular member onto the shaft.

16. The method of claim 15, wherein the step of sliding said tubular member over said shaft further includes the step of providing said tubular member and said shaft comprised of a material from the group consisting of oil-filled thermoplastic rubbers, and those including a composition of a thermoplastic rubber block copolymer, a crosslinkable organic silicone elastomer and a hydrophobic oil-type plasticizer.

17. The method of claim 15, wherein the step of installing shrink tubing further includes the step of providing shrink tubing comprising a fluorinated polyolefin including a pigment.

18. The method of claim 15, further including the step of placing a heat curable adhesive between the shaft and the tubular member.

19. The method of claim 15, further including the step of removing the shrink tubing from the shaft after the sealing step.

* * * * *